US008722953B2

(12) United States Patent
Brehme et al.

(10) Patent No.: US 8,722,953 B2
(45) Date of Patent: May 13, 2014

(54) METHOD FOR PRODUCING DIENES BY HYDRODIMERIZATION

(75) Inventors: Volker Brehme, Nottuln-Appelhuelsen (DE); Manfred Neumann, Marl (DE); Frank Bauer, Iserlohn (DE); Elke Fiebig-Bauer, Iserlohn (DE); Franz Rudolf Bauer, Iserlohn (DE); Johanna Elisabeth Bauer, Iserlohn (DE); Dirk Roettger, Antwerpen (BE)

(73) Assignee: Evonik Degussa GmbH, Essen (DE)

( * ) Notice: Subject to any disclaimer, the term of this patent is extended or adjusted under 35 U.S.C. 154(b) by 722 days.

(21) Appl. No.: 12/307,331

(22) PCT Filed: Jun. 6, 2007

(86) PCT No.: PCT/EP2007/055540
§ 371 (c)(1),
(2), (4) Date: Jan. 2, 2009

(87) PCT Pub. No.: WO2008/003559
PCT Pub. Date: Jan. 10, 2008

(65) Prior Publication Data
US 2009/0287032 A1 Nov. 19, 2009

(30) Foreign Application Priority Data

Jul. 5, 2006 (DE) .................... 10 2006 031 413
May 18, 2007 (DE) .................... 10 2007 023 515

(51) Int. Cl.
C07C 2/40 (2006.01)

(52) U.S. Cl.
USPC ........... 585/601; 585/500; 585/502; 585/510; 585/511

(58) Field of Classification Search
USPC ......... 585/502, 506, 507, 508, 510, 511, 500, 585/601
See application file for complete search history.

(56) References Cited

U.S. PATENT DOCUMENTS

| | | | | |
|---|---|---|---|---|
| 4,334,117 | A | | 6/1982 | Yoshimura et al. |
| 5,345,007 | A | * | 9/1994 | Monflier et al. ............ 568/909.5 |
| 5,545,786 | A | * | 8/1996 | Winter et al. .................. 585/435 |
| 5,728,839 | A | * | 3/1998 | Herrmann et al. ............ 548/103 |
| 7,026,523 | B2 | | 4/2006 | Roettger et al. |
| 7,115,790 | B2 | | 10/2006 | Beller et al. |
| 7,368,621 | B2 | | 5/2008 | Krissmann et al. |
| 7,371,909 | B2 | | 5/2008 | Beller et al. |
| 2004/0242947 | A1 | * | 12/2004 | Beller et al. .................. 585/527 |
| 2005/0065387 | A1 | * | 3/2005 | Beller et al. .................. 585/324 |
| 2005/0240039 | A1 | | 10/2005 | Rottger et al. |
| 2006/0058514 | A1 | | 3/2006 | Rottger et al. |
| 2007/0213574 | A1 | | 9/2007 | Borgmann et al. |
| 2008/0021234 | A1 | | 1/2008 | Nierlich et al. |

FOREIGN PATENT DOCUMENTS

| | | | |
|---|---|---|---|
| DE | 30 34 098 | 4/1981 | |
| DE | 30 24 878 | 1/1982 | |
| DE | 30 24 879 | 1/1982 | |
| DE | 30 24 877 | 2/1982 | |
| DE | 44 47 066 | 7/1996 | |
| DE | 101 28 144 | 12/2002 | |
| DE | 101 49 347 | 4/2003 | |
| DE | 10 2005 036 038 | 3/2006 | |
| DE | 102005036038 | * 3/2006 | .............. C07C 11/12 |
| DE | 102005036038 A1 | * 3/2006 | .............. C07C 11/12 |
| EP | 0 004 408 | 10/1979 | |
| EP | 0 004 410 | 10/1979 | |
| EP | 0 007 666 | 2/1980 | |
| EP | 0 008 139 | 2/1980 | |
| EP | 0 012 472 | 6/1980 | |
| EP | 0 012 475 | 6/1980 | |
| EP | 0 704 417 | 4/1996 | |
| JP | 9 87207 | 3/1997 | |
| WO | 2005 047217 | 5/2005 | |
| WO | 2005 047218 | 5/2005 | |

OTHER PUBLICATIONS

Machine translation of DE 102005036038 A1.*
Machine Translation of Borgmann, et al. (DE 102005036038 A1).*
Tsuji, et al., "Palladium Catalyzed Reaction of Butadiene and Isoprene" in Advances in Organometallic Chemistry, 17, 141-193 (1979)—month unknown.*
Kaneda, et al., "Selective Telomerization of Butadiene with Various Nucleophiles Catalyzed by Polymer-Bound Palladium(0) Complexes" in J. Org. Chem., (1981), 46, 2356-2362)—month unknown.*
Kaneda, K. et al., "Selective Telomerization of Butadiene With Various Nucleophiles Catalyzed by Polymer-Bound Palladium(0) Complexes", J. Org. Chem., vol. 46, No. 11, pp. 2356-2362 (1981).
Harkal, S. et al., "Development of a Highly Selective and Efficient Catalyst for 1,3-Butadiene Dimerization", Organic Letters, vol. 7, No. 4, pp. 541-544 (2005).
Gardner, S. et al., "Platinum-Metal Catalysed Formation of Linear Octadienes", Tetrahedron Letters, No. 2, pp. 163-164 (1972).
Roffia, P. et al., "Catalysis by Palladium Salts IV. Selective Hydrogenation With Formic Acid in the Palladium Catalysed Dimerisation of 1,3-Butadiene Syntheses of 1,7-Octadiene", Journal of Organometallic Chemistry, vol. 55, pp. 405-407 (1973).
Pittman, Jr. C. et al.,"Selective Hydrodimerization of 1,3-Butadiene to 1,7-Octadiene", Journal of Molecular Catalysis, vol. 15, pp. 377-381 (1982).
Jackstell, R. et al., "An Industrially Viable Catalyst System for Palladium-Catalyzed Telomerizations of 1,3-Butadiene With Alcohols", Chem. Eur. J., vol. 10, pp. 3891-3900 (2004).
Herrmann, W. et al., "N-Heterocyclische Carbene", Angew. Chem., vol. 109, pp. 2257-2282 and 2163-2187 (1997) (with English translation).
Boehm, V. P.W. et al., "N-Heterocyclic Carbenes Part 26. N-Heterocyclic Carbene Complexes of Palladium(0): Synthesis and Application in the Suzuki Cross-Coupling Reaction", Elsevier, Journal of Organometallic Chemistry, vol. 595, pp. 186-190 (2000).
U.S. Appl. No. 11/574,018, filed Feb. 21, 2007, Borgmann, et al.

* cited by examiner

Primary Examiner — In Suk Bullock
Assistant Examiner — Bradley Etherton
(74) Attorney, Agent, or Firm — Oblon, Spivak, McClelland, Maier & Neustadt, L.L.P.

(57) ABSTRACT

The invention relates to a process for preparing substituted or unsubstituted 1,7-diolefins by hydrodimerizing non-cyclic olefins having at least two conjugated double bonds in the presence of a reducing agent and of a catalyst, wherein the catalyst used is a metal-carbene complex.

22 Claims, No Drawings

METHOD FOR PRODUCING DIENES BY HYDRODIMERIZATION

The present invention relates to a process for preparing substituted or unsubstituted 1,7-diolefins by hydrodimerizing non-cyclic olefins having at least two conjugated double bonds in the presence of a reducing agent and of a metal-carbene complex.

1,7-Octadiene is used as a comonomer or for the subsequent crosslinking of polyolefins for the production of plastics. In addition, substituted or unsubstituted 1,7-diolefins constitute valuable starting materials for the production of α,ω-diols or α,ω-diamines or sebacic acid, which are in turn of interest for the preparation of polyesters or polyamides or alkyd resins. Moreover, 1,7-octadiene serves as a reactant for the preparation of 1-octene—a comonomer for plastics production.

Processes for preparing 1,7-octadiene from 1,3-butadiene by means of hydrodimerization are described by numerous publications.

Gardner et al. describe, in Tetrahedron Lett. 2 (1972) 163-164, the reaction of 1,3-butadiene with formic acid in the presence of various catalysts, for example diacetopalladium (II)(Pd(OAc)$_2$), Li$_2$PtCl$_4$ or palladium complexes with phosphine ligands, to give 1,6-octadiene. It is likewise stated that, in a reaction of 1,3-butadiene with formic acid in dimethylformamide and in the presence of an Li$_2$PtCl$_4$ catalyst, up to 80% of 1,7-octadiene is formed.

Roffia et al. describe, in J. Organomet. Chem. 55 (1973) 405-407, likewise the reaction of 1,3-butadiene with formic acid. The catalyst precursor used is (PPh$_3$)PdCl$_2$ which is reduced under the reaction conditions specified. The product obtained is a mixture of 1,3,7-octatriene, 1,7-octadiene and 1,6-octadiene. In J. Mol. Catal., 15 (1982) 377-381, Pittmann et al. describe the use of catalysts based on palladium with phosphine ligands for the preparation of 1,7-octadiene. The highest selectivity of 93% based on 1,7-octadiene is achieved here when triethylphosphine ligands are used.

EP 0 004 408 B1 and EP 0 004 410 B1 describe a process for preparing 1,7-octadiene from 1,3-butadiene in the presence of a palladium-phosphine catalyst. EP 0 004 410 additionally describes the use of palladium, platinum or rhodium on an inert support material as a cocatalyst.

EP 0 007 666 B1 likewise describes a process for preparing 1,7-octadiene from 1,3-butadiene in the presence of a palladium-phosphine catalyst; this process features the use of formates as a reducing agent.

EP 0 012 472 and EP 0 012 475 disclose a process in which 1,7-octadiene is prepared in the presence of a palladium catalyst and tertiary organophosphorus compounds, for example organophosphonites or organophosphinites or mixtures thereof, from 1,3-butadiene and formic acid or formates.

EP 0 008 139 B1 describes a process for preparing 1,7-octadiene from 1,3-butadiene in the presence of a palladium catalyst, tertiary phosphines and of a solvent selected from dialkyl sulphoxides and dialkylformamides, in the absence of a base.

The two published specifications DE 30 24 877 A1 and DE 30 24 878 A1 describe a process for hydrodimerizing 1,3-butadiene to 1,7-octadiene by means of a palladium-phosphine catalyst, the reducing agent used being hydrogen or a hydrogen-carbon dioxide mixture.

The published specification DE 30 24 879 A1 describes a process for hydrodimerizing 1,3-butadiene to 1,7-octadiene by means of a palladium-phosphine catalyst and a reducing agent, the solvent used being an oxygen-containing nitrogen heterocycle. After the distillative removal of the 1,7-octadiene, the catalyst-containing distillation bottoms are returned to the hydrodimerization.

The published specification DE 30 34 098 A1 describes a process for preparing alkadienes by hydrodimerizing 1,3-butadiene or isoprene in the presence of a palladium or platinum catalyst in a sulpholane solution, the reaction mixture comprising tertiary alkylamine formates and phosphine compounds. Here too, the catalyst is removed after the hydrodimerization and then returned to the hydrodimerization.

JP 09-087207 A describes the dimerization of alkadienes, for example 1,3-butadiene, in the presence of a reducing agent and of a palladium phosphinite catalyst. In this case, yields of 94.7% of octadiene are achieved, the purity of the 1,7-octadiene being 97.1%.

EP 0 704 417 A2 describes a process for preparing octadienes from 1,3-butadiene and formic acid in the presence of a palladium catalyst having phosphorus ligands, the pressure of the system being not more than the vapour pressure of the butadiene. The quantitative ratio of 1,7-octadiene to 1,6-octadiene in the product is 89:11.

DE 101 49 347 A1 discloses a process for preparing 1-octene in a two-stage process. In the first step, 1,3-butadiene is converted in the presence of a telomerization catalyst and of a reducing agent to 1,7-octadiene; in the second step, the 1,7-octadiene is partially hydrogenated to 1-octene. The telomerization catalysts described are numerous nickel, rhodium, palladium and platinum compounds, also including Pd(0) compounds with carbene ligands. Suitable carbene ligands mentioned include 1,3-disubstituted 2,3-dihydro-1H-imidazol-2-ylidenes, 1,3-disubstituted 4,5-dihydro-1H-triazol-5-ylidenes and, in some cases, 2,3-dihydrothiazol-2-ylidenes.

WO 2005/047217 and WO 2005/047218 each disclose a process for preparing 1-octene in a two-stage process. In the first process step, 1,3-butadiene is converted in the presence of a palladium complex which comprises one or more trisubstituted monodentate phosphorus compounds and of a hydrogen donor in an aprotic polar solvent to 1,7-octadiene.

DE 101 28 144 A1 discloses a process for telomerizing non-cyclic olefins having at least two conjugated double bonds with nucleophiles, the catalyst used being a palladium-carbene complex.

A telomerization is understood to mean the reaction of olefins with conjugated double bonds in the presence of nucleophiles. The products formed are compounds which are formed from two equivalents of the diene and one equivalent of the nucleophile, the product being a mixture of a plurality of compounds—as shown by Reaction Scheme 1.

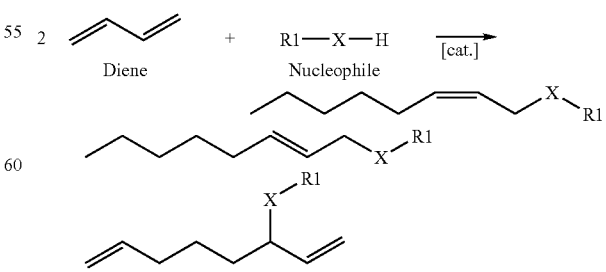

The main products formed in a telomerization are 1-substituted 2,7-octadienes; the by-products formed here are 3-substituted 1,7-octadienes. When telomerization catalysts modified with carbene ligands are used, ratios of main product to by-product of up to 98:2 are achieved (Chem. Eur. J. 10 (2004) 3891-3900).

In contrast, in a hydrodimerization, two equivalents of an olefin having conjugated double bonds are converted in the presence of a reducing agent according to Reaction Scheme 2:

Reaction Scheme 2

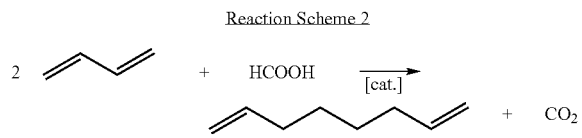

The reducing agent used in a hydrodimerization serves as a hydrogen provider; in the case of formic acid as the reducing agent, the co-product formed is carbon dioxide. The main product of the hydrodimerization of 1,3-butadiene is 1,7-octadiene.

The processes for hydrodimerizing 1,3-butadiene to 1,7-octadiene in the presence of phosphorus-modified palladium catalysts have low productivity (TON), activity (TOF) and/or selectivity, these being defined as follows:

$TON = n(\text{product})/n(\text{catalyst})$ or $TOF = n(\text{product})/[n(\text{catalyst})*\text{time}]$ $\text{Selectivity} = n(\text{product})/[n(\text{product})+n(\text{by-products})]$.

Generally, trivalent phosphorus compounds are oxygen-sensitive and are easily oxidized to the corresponding pentavalent phosphorus species, which is accompanied by deactivation of the catalyst. Owing to their high sensitivity, the recycling of these phosphorus-modified palladium catalysts is performable with difficulty and industrially only with large losses of activity. Palladium(II)-phosphine complexes are reduced under the reaction conditions of the hydrodimerization to form thermally unstable intermediates. When palladium complexes are modified with trialkylphosphines, this forms active catalysts which are selective for the 1,7-octadiene. Trialkylphosphines are, however, pyrophoric, expensive and difficult to use on the industrial scale. The triarylphosphines, which can be handled better, exhibit, in comparison to the trialkylphosphines, a significantly poorer selectivity in the hydrodimerization. In the prior art processes, these phosphine compounds are added to the hydrodimerization in excess. In the handling of phosphonites and phosphinites too in industrial scale plants, precautionary measures have to be taken, since these compounds are hydrolysis- and acid-sensitive. The use of formic acid or formic acid derivatives in the hydrodimerization has a correspondingly adverse effect on the stability of phosphonite or phosphinite-modified catalysts.

It was therefore an object of the present invention to provide a process for preparing substituted or unsubstituted 1,7-diolefins by hydrodimerization, which features simplified handling of the catalyst and also a high catalyst productivity. In particular, high selectivities with regard to the substituted or unsubstituted 1,7-octadiene should be achieved.

It has been found that, surprisingly, substituted or unsubstituted 1,7-diolefins can be prepared by hydrodimerizing non-cyclic olefins having at least two conjugated double bonds in the presence of a reducing agent and of a catalyst by a novel process, wherein the catalyst used is a metal-carbene complex which has a metal of group 8 to 10 of the Periodic Table and at least one carbene ligand. The process according to the invention has an improved selectivity and also a higher productivity compared to prior art processes. In the process according to the invention, for example in the hydrodimerization of 1,3-butadiene with formic acid, catalyst productivities of greater than 10 000 can be realized. In particular, it was found that, in the case of use of stabilizers for the non-cyclic olefins selected from alkylated phenols and stable N-oxyl radicals, smaller amounts of catalyst are required in comparison to the use of 4-tert-butylcatechol—the stabilizer according to the prior art. Moreover, this process variant of the process according to the invention features low by-product formation. The process according to the invention thus has a higher process reliability compared to prior art processes, and also a high catalyst productivity.

The invention provides a process for preparing substituted or unsubstituted 1,7-diolefins by hydrodimerizing non-cyclic olefins having at least two conjugated double bonds in the presence of a reducing agent and of a catalyst, characterized in that the catalyst used is a metal-carbene complex which has a metal of group 8 to 10 of the Periodic Table and at least one carbene ligand of the structure 1, 2, 3 or 4

(1)

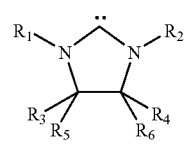

(2)

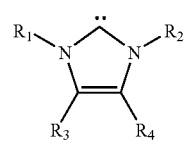

(3)

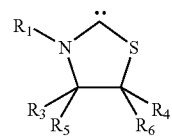

(4)

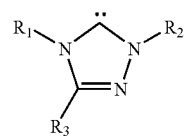

where:
$R_1, R_2 = -(CH_2)_n-B$
B = mono- or polycyclic aryl group having 6 to 14 carbon atoms or mono- or polycyclic heterocycle having 5 to 14 carbon atoms and heteroatoms, where this heterocycle has 1 to 3 heteroatoms selected from the group of N, O and S,
n = 0-4
$R_3, R_4, R_5$ and $R_6$ = hydrogen, alkyl, heteroaryl, aryl, —CN, —COOH, —COO-alkyl, —COO-aryl, —OCO-alkyl, OCO-aryl, —OCOO-alkyl, OCOO-aryl, —CHO, —CO-alkyl, —CO-aryl, —NH$_2$, —NH(alkyl), —N(alkyl)$_2$, NH(aryl), —N(aryl)$_2$, —F, —Cl, —Br, —I, —OH, —CF$_3$, —NO$_2$, -ferrocenyl, —SO$_3$H, —PO$_3$H$_2$, where the alkyl groups have 1 to 12 carbon atoms and the aryl groups 5 to 14 carbon atoms, and the substituents of the $R_3$ and $R_4$ type may also be part of a bridging aliphatic or aromatic ring, and the substituents of the $R_1$ and $R_2$ type are the same or different and are substituted or unsubstituted, and the substituents of the $R_3$, $R_4$, $R_5$ and $R_6$ type are likewise the same or different and are substituted or unsubstituted.

In the process according to the invention for preparing substituted or unsubstituted 1,7-diolefins by hydrodimerizing non-cyclic olefins having at least two conjugated double bonds in the presence of a reducing agent and of a catalyst, the catalyst used is a metal-carbene complex which has a metal of group 8 to 10 of the Periodic Table and at least one carbene ligand of the structure 1, 2, 3 or 4

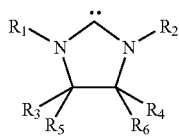

(1)

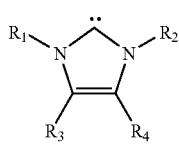

(2)

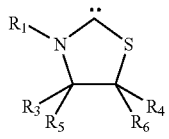

(3)

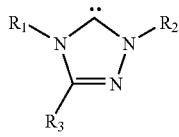

(4)

where:

$R_1$, $R_2$=—$(CH_2)_n$—B

B=mono- or polycyclic aryl group having 6 to 14 carbon atoms or mono- or polycyclic heterocycle having 5 to 14 carbon atoms and heteroatoms, where this heterocycle has 1 to 3 heteroatoms selected from the group of N, O and S, but preferably monocyclic aryl group having 6 carbon atoms, n=0-4, preferably 0-1, more preferably 0, $R_3$, $R_4$, $R_5$ and $R_6$=hydrogen, alkyl, heteroaryl, aryl, —CN, —COOH, —COO-alkyl, —COO-aryl, —OCO-alkyl, OCO-aryl, —OCOO-alkyl, OCOO-aryl, —CHO, —CO-alkyl, —CO-aryl, —NH$_2$, —NH(alkyl), —N(alkyl)$_2$, NH(aryl), —N(aryl)$_2$, —F, —Cl, —Br, —I, —OH, —CF$_3$, —NO$_2$, -ferrocenyl, —SO$_3$H, —PO$_3$H$_2$, where the alkyl groups have 1 to 12 carbon atoms and the aryl groups 5 to 14 carbon atoms, and the substituents of the $R_3$ and $R_4$ type may also be part of a bridging aliphatic or aromatic ring, and the substituents of the $R_1$ and $R_2$ type are the same or different and are substituted or unsubstituted, and the substituents of the $R_3$, $R_4$, $R_5$ and $R_6$ type are likewise the same or different and are substituted or unsubstituted.

In the context of this invention, substituted or unsubstituted 1,7-diolefins are understood to mean compounds of the structure 9:

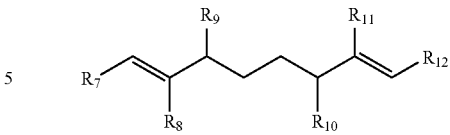

(9)

where $R_7$ to $R_{12}$ are each independently hydrogen, an alkyl group, which in particular has 1 to 4 carbon atoms, preferably one carbon atom, or a halogen group, especially chlorine.

In a particular embodiment of the process according to the invention, the metal-carbene complexes have carbene ligands with substituents of the $R_1$, $R_2$, $R_3$, $R_4$, $R_5$ or $R_6$ type, which have at least one substituent from the group of H, —CN, —COOH, —COO-alkyl, —COO-aryl, —OCO-alkyl, OCO-aryl, —OCOO-alkyl, OCOO-aryl, —CHO, —CO-alkyl, —CO-aryl, —NH$_2$, —NH (alkyl), —N (alkyl)$_2$, NH (aryl), —N(aryl)$_2$, —F, —Cl, —Br, —I, —OH, —CF$_3$, —NO$_2$, -ferrocenyl, —SO$_3$H, —PO$_3$H$_2$, where the alkyl groups contain 1 to 12 carbon atoms and the aryl groups 5 to 14 carbon atoms.

In the process according to the invention, preference is given to using metal-carbene complexes which have a metal selected from nickel, rhodium, palladium and/or platinum. However, particular preference is given to using metal-carbene complexes which have palladium as the metal.

In the context of this invention, carbene ligands are understood to mean both free carbenes which can function as ligands and carbenes coordinated to the metal. In the process according to the invention, preference is given to using metal-carbene complexes which have at least one carbene ligand selected from structures 1 to 4 where $R_3$ to $R_6$=hydrogen. The metal-carbene complexes used preferably have at least one carbene ligand of the structure 2 where $R_3$ and $R_4$ are each hydrogen. Particular preference is given to using metal-carbene complexes which have at least one carbene ligand of the structure 2 where $R_3$ and $R_4$ are each hydrogen and $R_1$ and $R_2$, where n=0, and B are each a phenyl or 2,4,6-trimethylphenyl group.

Examples of carbene ligands which correspond to the general structures 1 or 2, and complexes which contain such ligands, are already described in the technical literature (W. A. Herrmann, C. Köcher, Angew. Chem. 1997, 109, 2257; Angew, Chem. Int. Ed. Engl. 1997, 36, 2162; V. P. W. Böhm, C. W. K. Gstöttmayr, T. Weskamp, W. A. Herrmann, J. Organomet. Chem. 2000, 595, 186; DE 44 47 066).

The catalyst metal, which is preferably palladium and with which the active catalysts form under the reaction conditions, can be introduced into the process according to the invention in various ways:

a.) as a palladium-carbene complex, where the palladium is present preferably in the (II) or (0) oxidation states, b.) in the form of precursors from which the catalysts are formed in situ. This can be done by widening the ligand sphere or by breaking up bridge structures, proceeding from metal salts or metal complexes. A further possibility is the exchange of ligands which coordinate on the central metal by the carbene ligands. Preference is given here to using palladium(0) and/or palladium(II) compounds; particular preference is given to using palladium(II)acetate, palladium(II) acetyl-acetonate and/or bis(dibenzylideneacetone)palladium (0). The carbene ligands of the structures 1 to 4 are used in the form of free carbenes or as metal complexes, or obtained in situ from carbene precursors. Suitable carbene precursors are, for example, salts of the carbenes of structures 5 to 8

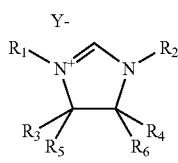

(5)

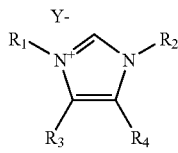

(6)

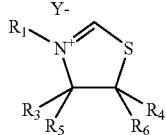

(7)

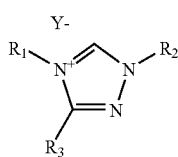

(8)

where the substituents of the $R_1$ to $R_6$ type are each as defined in the structures 1 to 4, and Y is a singly charged anionic group or, according to the stoichiometry, a proportionate amount of a multiply charged anionic group.

Examples of Y are halides, hydrogensulphate, sulphate, alkylsulphates, arylsulphates, borates, hydrogen-carbonate, carbonate, alkylcarboxylates, aryl-carboxylates. It is possible to release the corresponding carbenes from the salts of the carbenes, for example, by reaction with a base. Suitable bases are, for example, metal hydrides, metal alkoxides, carbonyl metallates, metal carboxylates, metal amides or metal hydroxides.

The amount is highly dependent upon the type of base used. In metal-carbene complexes, preference is given to using 0 to 50 000 mol of base per mole of metal, preferably 0.5 to 5000 mol, more preferably 0.5 to 500 mol of base per mole of metal. It is also possible to use a mixture of a plurality of bases.

The concentration of the catalyst, reported in a formal sense in ppm (mass) of metal based on the overall mass of the reaction mixture is, at the start of the hydrodimerization in the process according to the invention, preferably 0.01 ppm to 5000 ppm, preferentially 0.1 to 1000 ppm, more preferably 0.1 to 500 ppm and most preferably 1 to 100 ppm. In a particular embodiment of the process according to the invention, this concentration of the catalyst may be 1 to 50 ppm. The ratio [mol/mol] of carbene ligand to metal is preferably 0.01:1 to 250:1, preferably 0.1:1 to 100:1, more preferably 1:1 to 20:1.

The carbene ligand can be supplied to the reaction in bulk, dissolved or in the form of metal complexes. An additional ligand can be supplied to the reaction at any time and at any point in the reactor, in bulk, as a solution or in the form of a metal complex. This additional ligand may likewise be a carbene or a carbene precursor, or else belong to another class of ligands, for example phosphorus ligands, especially triphenylphosphine. In the process according to the invention, preference is given to using catalysts which do not have any phosphorus ligands; particular preference is given to using catalysts which have exclusively carbene ligands, and very particular preference to using catalysts which have exclusively carbene ligands of the structures 1, 2, 3 or 4.

After the hydrodimerization process, the catalyst can be removed and recycled for a new reaction. This removal can be effected, for example, by means of a distillation, extraction, precipitation or adsorption. When the catalyst is present completely or partly in a second phase, this can be done by a simple separation of the phases.

Owing to the catalyst activities and stabilities, it is possible in the process according to the invention to use extremely small amounts of catalyst. As a result, there exists the option of not needing to recycle the catalyst owing to the low concentrations in the reaction mixture.

When a metal-carbene complex whose oxidation number is >0 is used, this complex may optionally be pre-reduced before the hydrodimerization. The reducing agent used for this purpose may be identical to the reducing agent used in the hydrodimerization. Possible reducing agents are, for example, formic acid, formates, hydrogen, alkali metal borohydrides, alkali metal aluminium hydrides or boranes.

In the process according to the invention, preference is given to using non-cyclic olefins having at least two conjugated double bonds, selected from 1,3-butadiene, isoprene, 1,3-pentadiene, chloroprene, or corresponding mixtures which comprise non-cyclic olefins having at least two conjugated double bonds, as arise, for example, from a cracking process. Preference is given to using 1,3-butadiene in the process according to the invention.

The non-cyclic olefins having at least two conjugated double bonds may be used in stabilized or unstabilized form. Suitable stabilizers are preferably free-radically active inhibitors, for example alkylated phenols, alkylated catechols or stable N-oxyl radicals. In particular, in the process according to the invention, non-cyclic olefins which have either no stabilizer or a stabilizer selected from alkylated phenols or stable N-oxyl radicals are used. In the process according to the invention, preference is given to using non-cyclic olefins which have, as a stabilizer, alkylated phenols or stable N-oxyl radicals. Particular preference is given to stable N-oxyl radicals as stabilizers, for example 4-substituted or unsubstituted 2,2,6,6-tetramethylpiperidine N-oxyls, especially 4-hydroxy-2,2,6,6-tetramethylpiperidine N-oxyl or 2,2,6,6-tetramethylpiperidine N-oxyl. The stabilizer may also be added to the reaction mixture in the process according to the invention separately from the non-cyclic olefins.

The reducing agents used in the process according to the invention may be formic acid, formates and/or hydrogen; preference is given to using formic acid. Examples of formates are ammonium formate, organic salts, for example triethylammonium formate, trimethyl-ammonium formate, tripropylammonium formate and alkali metal and alkaline earth metal salts, especially lithium formate, sodium formate, potassium formate, magnesium formate and calcium formate. The formates may be added to the reaction in bulk or in the dissolved form or be prepared in situ. For instance, the alkali metal formates can be prepared from the reaction of formic acid with the metal hydroxides, but may also be prepared from metal hydroxides and carbon monoxide. The carbon monoxide sources used may be gases comprising carbon monoxide, for example synthesis gas ($H_2$/CO mixture).

To form one mole of 1,7-octadiene from two moles of butadiene, one mole of formic acid or formate is required (stoichiometry of the reaction). Depending on the reaction, the entire amount and optionally an excess of reducing agent can be added completely at the start of the reaction. Alternatively, the reducing agent can be metered in the course of the reaction. When formic acid is used as the reducing agent in the process according to the invention, the formic acid should be metered in the course of the reaction. When the formic acid is initially charged, a deactivation of the catalyst can be observed.

When hydrogen is used as the reducing agent, the partial pressure is preferably 1 to 300 bar, preferentially 1 to 64 bar. The hydrogen is used preferably in pure form or in mixtures with other gases, for example carbon dioxide or nitrogen.

It is possible to use a plurality of reducing agents alongside one another, for example formic acid and hydrogen.

In the process according to the invention, the ratio [mol/mol] between non-cyclic olefin having at least two conjugated double bonds used and reducing agent is preferably 1:1 to 10:1, preferentially 2:1 to 4:1 and more preferably 2:1 to 3:1.

In the process according to the invention, preference is given to using solvents which are inert under the reaction conditions, or exhibit substantially inert behaviour. Suitable solvents include aliphatic, cycloaliphatic and aromatic hydrocarbons, amines, for example pyridine and 2,6-lutidine, amides, for example N-methylpyrrolidine, acetamide, N,N-dimethylformamide, N,N-dimethylacetamide, nitriles, for example acetonitrile and benzonitrile, ketones, for example acetone and methyl ethyl ketone, carboxylic esters, for example ethyl acetate, ethers, for example methyl tert-butyl ether, tetrahydrofuran, dioxane, anisole, alkyl and aryl ethers of ethylene glycol, diethylene glycol and polyethylene glycol, and other polar solvents, for example dimethyl sulphoxide, 1,3-dimethyl-2-imidazolidinone, 1,3-dimethyl-3,4,5,6-tetrahydro-2(1H)-pyrimidinone, sulpholane, propylene carbonate or tetrahydrothiophene oxide. Ionic liquids, for example imidazolium or pyridinium salts, may also be used as solvents. The solvents may be used alone or else as mixtures of different solvents. In the process according to the invention, preference is given to using solvents which have a relative dielectric constant of 30 to 100 (at a temperature of 20° C.), especially solvents selected from N-methylpyrrolidone, N,N-dimethylformamide, dimethyl sulphoxide and dimethylacetamide.

It is often advantageous to perform the hydrodimerization in the presence of bases. Examples of suitable bases are metal hydroxides, especially alkali metal hydroxides and alkaline earth metal hydroxides, metal carbonates and metal hydrogencarbonates, especially alkali metal and alkaline earth metal carbonates and alkali metal and alkaline earth metal hydrogencarbonates, hydroxides of quaternary ammonium or phosphonium ions, alkoxides, enolates, phenoxides, metal salts of carboxylic acids, metal amides, for example sodium amide or lithium diethylamide, and organic nitrogen bases, especially amines, for example triethylamine, trioctylamine or pyridine. It is also possible to use carbon dioxide as the base. Preference is given to using alkali metal hydroxides, alkali metal alkoxides or tertiary amines as bases in the process according to the invention.

The amount of base used which can be added to the hydrodimerization is highly dependent upon the type of base used. In the process according to the invention, preference is given to using 0 mol % to 100 mol %, preferably 0 mol % to 50 mol %, more preferably 0 mol % to 20 mol % and most preferably 0 mol % to 10 mol %, of basic component, based on the olefin used. It is also possible to use a mixture of a plurality of bases in the process according to the invention.

For the process according to the invention, it is advantageous when no acidic components are present in the reaction mixture, since they lead to the increased formation of by-products by isomerization. This can be ensured by the use of neutral reducing agents, for example hydrogen or formates.

In the case of use of pure formic acid as a reducing agent, an equimolar amount of a base, for example triethylamine, can be added. Preference is given to a process according to the invention in which the formic acid reducing agent is reacted completely without or with a substoichiometric amount of base; this means a stoichiometric ratio of base to formic acid of 0:1 to 1:1. Particular preference is given to the embodiment in which formic acid is metered in at reaction temperature, which results, owing to the high reaction rate, in a spontaneous reaction, and formic acid cannot become enriched in the reaction mixture. In this case, the amount of base required is significantly reduced, or it can even be dispensed with entirely.

In the process according to the invention, the hydrodimerization is performed preferably under a pressure of 1 to 100 bar and preferentially of 6 to 25 bar.

The temperature during the hydrodimerization in the process according to the invention is preferably 20 to 160° C., preferably 60 to 120° C. and more preferably 70 to 100° C.

The process according to the invention can be operated continuously or batchwise, and is not restricted to the use of particular reactor types. Examples of reactors in which the reaction can be performed are stirred tank reactors, stirred tank batteries, flow tubes and loop reactors. Combinations of different reactors are also possible, for example a stirred tank reactor with downstream flow tube.

The heat of reaction which arises in the reaction is removed by known processes, for example by means of internal or external coolers. Specifically, this may mean the use of tube bundle reactors, reactors with cooling fingers, cooling coils or plates, or the cooling of a recycle stream (reactors with circulation, recycling).

For the process according to the invention, it is not necessary to achieve complete conversion of the non-cyclic olefin in the hydrodimerization reaction. The conversion of the non-cyclic olefin is therefore preferably 40% to 100%, more preferably 60% to 99%, most preferably 85% to 98%. In the case of complete conversion of the non-cyclic olefin in the process according to the invention, there may be increased formation of by-products, since the reducing agent is no longer depleted completely. In the case of use of formic acid as the reducing agent, this may lead to isomerization reactions. In the case of use of hydrogen as a reducing agent, hydrogenations can be observed in the case of complete conversion. The hydrodimerization in the process according to the invention is advantageously performed with the exclusion of oxygen, since oxygen promotes the polymerization of non-cyclic olefins having at least two conjugated double bonds and, as a result, lowers the yield of substituted or unsubstituted 1,7-diolefins.

The reactants of the process according to the invention can all be initially charged together and then the appropriate reaction conditions can be established. In a particular embodiment of the process according to the invention, the catalyst is first obtained in situ and then the stabilizer and the non-cyclic olefin are added and the appropriate reaction conditions are established thereafter. In particular, it is advisable in the process according to the invention to meter in the reducing agent in the course of the reaction and not to initially charge it—especially in the case of use of formic acid as a reducing agent. Even excessively rapid metered addition of the formic acid as a reducing agent can lead to lower yields of 1,7-diolefins.

The examples which follow are intended to further illustrate the process according to the invention without any intention that the invention be restricted to this embodiment.

EXAMPLE 1

Preparation of the carbene ligand bis(2,4,6-trimethylphenyl)imidazolium o-cresoxide-o-cresol 1,3-Bis(2,4,6-trimethylphenyl)imidazolium chloride is prepared by the process described in Organometallics 1999, 18, 529-533. The 1,3-bis(2,4,6-trimethylphenyl)imidazolium chloride prepared in this way is converted to the corresponding cresoxide as follows: 2.35 g of NaOH are dissolved in 45 g of water and then 12.7 g of molten o-cresol are added. This forms a milky grey liquid. This solution is added slowly with stirring to a solution of 20 g of 1,3-bis(2,4,6-trimethylphenyl) imidazolium chloride in 45 g of water. A light grey solid precipitates out, and is filtered off with a G4 frit. Subsequently, the solid is washed with a little water and methyl tert-butyl ether. After the drying, 18.9 g of bis(2,4,6-trimethylphenyl)imidazolium o-cresoxide-o-cresol are obtained, which corresponds to a yield of 91%.

EXAMPLE 2

100 ppm of Pd, 1,3-butadiene stabilized with 4-tert-butylcatechol

Under protective gas, 0.112 g of palladium acetate (47.5% Pd, from Acros), 0.312 g of 1,3-bis(2,4,6-trimethylphenyl) imidazolium o-cresoxide-o-cresol and 0.108 g of sodium methoxide (>97%, from Merck) are dissolved in 200 g of freshly distilled N-methyl-pyrrolidone (NMP, ≥99.5%, from Merck) and stirred at 50° C. for 1 hour. This mixture is sucked into an evacuated 2 l autoclave from Büchi and then 240 g of 1,3-butadiene (1,3-butadiene 2.6, stabilized with approx. 100 ppm of 4-tert-butylcatechol (TBC), from Oxeno Olefinchemie GmbH) are condensed in at −5° C. The amount is measured by means of the weighing of the pressurized gas bottle. Thereafter, a pressure of 11 bar is applied by means of argon and the reactor is heated to 75° C. Within 30 minutes, 101 g of formic acid (98-100%, from Riedel-de Haen) are metered in. The pressure is kept constant at 20 bar by means of a valve. An amount of offgas of 31.7 l is measured. The continued reaction time is 15 min. After the cooling and decompression of the autoclave, the product mixture is analysed by GC. After a one-stage distillation at 50 mbar and a maximum bottom temperature of 80° C., a further analysis is effected by means of GC. Table 1 shows the particular analysis results in GC area %.

TABLE 1

| | 1,3-Butadiene | 1,7-Octadiene | 1,6-Octadiene | 4-Vinyl-cyclohexene | N-Methyl-pyrrolidone | Further compounds |
|---|---|---|---|---|---|---|
| Reactor effluent | 2.1 | 69.4 | 1.6 | 0.1 | 26.7 | 0.1 |
| Distillate | 0 | 97.4 | 2.4 | 0.1 | 0 | 0.1 |
| Distillation bottoms | 0 | 6.2 | 0.3 | 0 | 92.7 | 0.8 |

The distillate obtained is 215.7 g of octadienes, which corresponds to an isolated yield of 89.3%. The purity based on 1,7-octadiene is 97.4%. The conversion of the formic acid is complete.

EXAMPLE 3

50 ppm of Pd, 1,3-butadiene stabilized with 4-tert-butylcatechol

Under protective gas, 0.056 g of palladium acetate, 0.26 g of 1,3-bis(2,4,6-trimethylphenyl)imidazolium o-cresoxide-o-cresol and 0.108 g of sodium methoxide are dissolved in 200 g of freshly distilled N-methyl-pyrrolidone and stirred at 50° C. for 1 hour. This mixture is sucked into an evacuated 2 l autoclave from Büchi and then 240 g of 1,3-butadiene (stabilized with approx. 100 ppm of 4-tert-butylcatechol) are condensed in at −5° C. The amount is measured by means of the weighing of the pressurized gas bottle. Thereafter, a pressure of 14 bar is applied by means of argon and the reactor is heated to 75° C. Within 30 minutes, 93 g of formic acid are metered in. The pressure is kept constant at 20 bar by means of a valve. An amount of offgas of <1 l is measured. The continued reaction time is 30 minutes. After the cooling and decompression of the autoclave, the product mixture is analysed by GC. Table 2 shows the particular analysis results in GC area %.

TABLE 2

| | 1,3-Butadiene | 1,7-Octadiene | 1,6-Octadiene | 4-Vinyl-cyclohexene | N-Methyl-pyrrolidone | Further compounds |
|---|---|---|---|---|---|---|
| Reactor effluent | 14.2 | 7.3 | 7.6 | 0.3 | 70.2 | 0.7 |

318.4 g of crude product mixture are obtained. The remaining amount of formic acid is 82.4 g (determined titrimetrically), i.e. the conversion is only 11% based on the formic acid used.

EXAMPLE 4

Not Inventive

Under protective gas, 0.112 g of palladium acetate, 0.134 g of 1,3-dimethylimidazolium iodide (prepared according to Example 1A in WO 97/34875) and 0.108 g of sodium methoxide are dissolved in 200 g of freshly distilled N-methylpyrrolidone and stirred at 50° C. for 1 hour. This mixture is sucked into an evacuated 2 l autoclave from Büchi and then 240 g of 1,3-butadiene (stabilized with approx. 100 ppm of 4-tert-butyl-catechol) are condensed in at −5° C. The amount is measured by means of the weighing of the pressurized gas bottle. Thereafter, a pressure of 14 bar is applied by means of argon and the reactor is heated to 75° C. Within 64 minutes, 101 g of formic acid are metered in. The pressure is kept constant at 20 bar by means of a valve. No offgas evolution is measured. After the cooling and decompression of the autoclave, the product mixture is analysed by GC. A compilation of the analysis results is shown in Table 3.

TABLE 3

| | 1,3-Butadiene | 1,7-Octadiene | 1,6-Octadiene | 4-Vinyl-cyclohexene | N-Methyl-pyrrolidone | Further compounds |
|---|---|---|---|---|---|---|
| Reactor effluent | 10.5 | 0 | 0 | 0.3 | 88.8 | 0.4 |

No 1,7-octadiene was detectable in the crude product mixture.

EXAMPLE 5

Not Inventive

Under protective gas, 0.112 g of palladium acetate, 0.109 g of 1,3-di-1-propylimidazolium chloride (>97%, from ABCR) and 0.108 g of sodium methoxide are dissolved in 200 g of freshly distilled N-methyl-pyrrolidone and stirred at 50° C. for 1 hour. This mixture is sucked into an evacuated 2 l autoclave from Büchi and then 240 g of 1,3-butadiene (stabilized with approx. 100 ppm of 4-tert-butylcatechol) are condensed in at −5° C. The amount is measured by means of the weighing of the pressurized gas bottle. Thereafter, a pressure of 11 bar is applied by means of argon and the reactor is heated to 75° C. Within 65 minutes, 101 g of formic acid are metered in. The pressure is kept constant at 20 bar by means of a valve. An amount of offgas of 2.9 l is measured. The continued reaction time is 30 minutes. After the cooling and decompression of the autoclave, the product mixture is analysed by GC. A compilation of the analysis results is shown in Table 4.

TABLE 4

| | 1,3-Buta-diene | 1,7-Octa-diene | 1,6-Octa-diene | 4-Vinyl-cyclohexene | N-Methyl-pyrrolidone | Further compounds |
|---|---|---|---|---|---|---|
| Reactor effluent | 14.4 | 0 | 0 | 0.5 | 85.1 | 0 |

No 1,7-octadiene was detectable in the crude product mixture.

EXAMPLE 6

Not Inventive

Under protective gas, 0.112 g of palladium acetate, 0.130 g of 1,3-di-tert-butylimidazolium chloride (>97%, from ABCR) and 0.108 g of sodium methoxide are dissolved in 200 g of freshly distilled N-methyl-pyrrolidone and stirred at 50° C. for 1 hour. This mixture is sucked into an evacuated 2 l autoclave from Büchi and then 240 g of 1,3-butadiene (stabilized with approx. 100 ppm of 4-tert-butylcatechol) are condensed in at −5° C. The amount is measured by means of the weighing of the pressurized gas bottle. Thereafter, a pressure of 11 bar is applied by means of argon and the reactor is heated to 75° C. Within 60 minutes, 101 g of formic acid are metered in. The pressure is kept constant at 20 bar by means of a valve. An amount of offgas of 2.8 l is measured. The continued reaction time is 30 minutes. After the cooling and decompression of the autoclave, the product mixture is analysed by GC. A compilation of the analysis results is shown in Table 5.

TABLE 5

| | 1,3-Buta-diene | 1,7-Octa-diene | 1,6-Octa-diene | 4-Vinyl-cyclohexene | N-Methyl-pyrrolidone | Further compounds |
|---|---|---|---|---|---|---|
| Reactor effluent | 10 | 0 | 0 | 0.4 | 89.2 | 0.4 |

No 1,7-octadiene was detectable in the crude product mixture.

EXAMPLE 7

Not Inventive

Under protective gas, 0.112 g of palladium acetate, 0.109 g of 1,3-di-tert-butylimidazolium-2-ylidene (98%, from Strem) and 0.108 g of sodium methoxide are dissolved in 200 g of freshly distilled N-methyl-pyrrolidone and stirred at 50° C. for 1 hour. This mixture is sucked into an evacuated 2 l autoclave from Büchi and then 240 g of 1,3-butadiene (stabilized with approx. 100 ppm of 4-tert-butylcatechol) are condensed in at −5° C. The amount is measured by means of the weighing of the pressurized gas bottle. Thereafter, a pressure of 14 bar is applied by means of argon and the reactor is heated to 75° C. Within 66 minutes, 101 g of formic acid are metered in. The pressure is kept constant at 20 bar by means of a valve. An amount of offgas of 3.42 l is measured. The continued reaction time is 30 minutes. After the cooling and decompression of the autoclave, the product mixture is analysed by GC. A compilation of the analysis results is shown in Table 6.

TABLE 6

| | 1,3-Buta-diene | 1,7-Octa-diene | 1,6-Octa-diene | 4-Vinyl-cyclohexene | N-Methyl-pyrrolidone | Further compounds |
|---|---|---|---|---|---|---|
| Reactor effluent | 11.7 | 0.2 | 0 | 0.5 | 87.1 | 0.5 |

Only 0.2 area % of 1,7-octadiene were detectable in the crude product mixture.

Examples 4-7 show clearly that not all metal-carbene complexes catalyze a hydrodimerization of 1,3-butadiene to 1,7-octadiene.

EXAMPLE 8

30 ppm of Pd, 1,3-butadiene stabilized with 100 ppm of 4-hydroxy-2,2,6,6-tetramethylpiperidine N-oxyl based on 1,3-butadiene Under protective gas, 0.056 g of palladium acetate, 0.521 g of 1,3-bis(2,4,6-trimethylphenyl)imidazolium o-cresoxide-o-cresol and 0.27 g of sodium methoxide are dissolved in 200 g of freshly distilled N-methyl-pyrrolidone, and the mixture is stirred at 50° C. for 1 hour and then cooled to 20° C. Subsequently, 0.32 g of 4-hydroxy-2,2,6,6-tetramethylpiperidine N-oxyl (SiYPro C710 from Degussa AG) is added. This mixture is sucked into an evacuated 2 l autoclave from Büchi and then 480 g of 1,3-butadiene (unstabilized) are condensed in at −5° C. The amount is measured by means of the weighing of the pressurized gas bottle. Thereafter, a pressure of 10 bar is applied by means of argon and the reactor is heated to 75° C. Within 120 minutes, 202 g of formic acid (98-100%) are metered in. After the reaction has set in, the temperature is kept between 80° C. and 90° C. The pressure is kept constant at 20 bar by means of a valve. An amount of offgas of 82.7 l is measured. The continued reaction time is 30 minutes. After the cooling and decompression of the autoclave, the product mixture is analysed by GC. After a one-stage distillation at 50 mbar and a maximum bottom temperature of 80° C., a further analysis is effected by means of GC. Table 7 shows the particular analysis results in GC area %.

TABLE 7

|  | 1,3-Butadiene | 1,7-Octadiene | 1,6-Octadiene | 4-Vinyl-cyclohexene | N-Methyl-pyrrolidone | Further compounds |
|---|---|---|---|---|---|---|
| Reactor effluent | 7.6 | 70.0 | 4.2 | 0.2 | 17.8 | 0.2 |
| Distillate | 0 | 94.3 | 5.5 | 0.2 | 0 | 0 |
| Distillation bottoms | 0 | 6.2 | 0.8 | 0.1 | 90.8 | 2.1 |

The distillate obtained is 336.3 g of octadienes, which corresponds to an isolated yield of 69.4%. The purity based on 1,7-octadiene is 94.3%. The conversion of the formic acid is complete.

EXAMPLE 9

28 ppm of Pd, base, 1,3-butadiene stabilized with 100 ppm of 4-hydroxy-2,2,6,6-tetramethylpiperidine N-oxyl based on 1,3-butadiene Under protective gas, 0.056 g of palladium acetate, 0.521 g of 1,3-bis(2,4,6-trimethylphenyl)imidazolium o-cresoxide-o-cresol and 0.27 g of sodium methoxide are dissolved in 200 g of freshly distilled N-methyl-pyrrolidone, and the mixture is stirred at 50° C. for 1 hour and then cooled to 20° C. Subsequently, 0.32 g of 4-hydroxy-2,2,6,6-tetramethylpiperidine N-oxyl (SiYPro C710 from Degussa AG) and 44.4 g of triethylamine as base are added. This mixture is sucked into an evacuated 2 l autoclave from Büchi and then 480 g of 1,3-butadiene (unstabilized) are condensed in at −5° C. The amount is measured by means of the weighing of the pressurized gas bottle. Thereafter, a pressure of 10 bar is applied by means of argon and the reactor is heated to 75° C. Within 123 minutes, 202 g of formic acid (98-100%) are metered in. After the reaction has set in, the temperature is kept between 80° C. and 90° C. The pressure is kept constant at 20 bar by means of a valve. An amount of offgas of 77 l is measured. The continued reaction time is 15 min. After the cooling and decompression of the autoclave, the product mixture is analysed by GC. After a distillation and the removal of two fractions at 50 mbar and a maximum bottom temperature of 80° C., a further analysis is effected by means of GC. Table 8 shows the particular analysis results in GC area %.

TABLE 8

|  | 1,3-Butadiene | Triethylamine | 1,7-Octadiene | 1,6-Octadiene | 4-Vinyl-cyclohexene | N-Methyl-pyrrolidone | Further compounds |
|---|---|---|---|---|---|---|---|
| Reactor effluent | 2.8 | 5.6 | 69.4 | 4.9 | 0.2 | 16.6 | 0.5 |
| Distillate 1 | 0 | 27.4 | 69.3 | 3.2 | 0.1 | 0 | 0 |
| Distillate 2 | 0 | 2.9 | 90.1 | 6.5 | 0.2 | 0.1 | 0.2 |
| Distillation bottoms | 0 | 0.7 | 5.6 | 1.0 | 0.1 | 89.5 | 3.1 |

In the distillates, 400.8 g of octadienes are obtained, which corresponds to a yield of 82.7%. The purity of the octadienes based on 1,7-octadiene is 93.5%. The conversion of the formic acid is complete.

EXAMPLE 10

15 ppm of Pd, 1,3-butadiene stabilized with 100 ppm of 4-hydroxy-2,2,6,6-tetramethylpiperidine N-oxyl based on 1,3-butadiene Under protective gas, 0.028 g of palladium acetate, 0.26 g of 1,3-bis(2,4,6-trimethylphenyl)imidazolium o-cresoxide-o-cresol and 0.13 g of sodium methoxide are dissolved in 200 g of freshly distilled N-methyl-pyrrolidone, and the mixture is stirred at 50° C. for 1 hour and then cooled to 20° C. Subsequently, 0.32 g of 4-hydroxy-2,2,6,6-tetramethylpiperidine N-oxyl (SiYPro C710 from Degussa AG) is added. This mixture is sucked into an evacuated 2 l autoclave from Büchi and then 480 g of 1,3-butadiene (unstabilized) are condensed in at −5° C. The amount is measured by means of the weighing of the pressurized gas bottle. Thereafter, a pressure of 10 bar is applied by means of argon and the reactor is heated to 80° C. Within 240 minutes, 193 g of formic acid (98-100%) are metered in. After the reaction has set in, the temperature is kept between 80° C. and 81° C. with the aid of an internal cooling coil. The pressure is kept constant at 20 bar by means of a valve. An amount of offgas of 71 l is measured. The continued reaction time is 10 minutes. After the cooling and decompression of the autoclave, the product mixture is analysed by GC. After a one-stage distillation at 100-50 mbar and a maximum bottom temperature of 80° C., a further analysis is effected by means of GC. Table 9 shows the particular analysis results in GC area %.

TABLE 9

|  | 1,3-Butadiene | 1,7-Octadiene | 1,6-Octadiene | 4-Vinyl-cyclohexene | N-Methyl-pyrrolidone | Further compounds |
|---|---|---|---|---|---|---|
| Reactor effluent | 1.8 | 77.0 | 2.6 | 0.3 | 18.2 | 0.1 |
| Distillate | 0 | 96.1 | 3.4 | 0.3 | 0.2 | 0 |
| Distillation bottoms | 0 | 6.4 | 0.5 | 0.1 | 91.9 | 1.1 |

The distillate obtained is 421.2 g of octadienes, which corresponds to an isolated yield of 94.7%. The purity based on 1,7-octadiene is 96.1%. The conversion of the formic acid is complete.

EXAMPLE 11

6 ppm of Pd, 1,3-butadiene stabilized with 100 ppm of 4-hydroxy-2,2,6,6-tetramethylpiperidine N-oxyl based on 1,3-butadiene Under protective gas, 0.0112 g of palladium acetate, 0.521 g of 1,3-bis(2,4,6-trimethylphenyl)imidazolium o-cresoxide-o-cresol and 0.13 g of sodium methoxide are dissolved in 200 g of freshly distilled N-methyl-pyrrolidone, and the mixture is stirred at 50° C. for 1 hour and then cooled to 20° C. Subsequently, 0.32 g of 4-hydroxy-2,2,6,6-tetramethylpiperidine N-oxyl (SiYPro C710 from Degussa AG) is added. This mixture is sucked into an evacuated 2 l autoclave from Büchi and then 480 g of 1,3-butadiene (unstabilized) are condensed in at −5° C. The amount is measured by means of the weighing of the pressurized gas bottle. Thereafter, a pressure of 10 bar is applied by means of argon and the reactor is heated to 80° C. Within 12 hours, 193 g of formic acid (98-100%) are metered in. After the reaction has set in, the temperature is kept between 80° C. and 81° C. with the aid of an internal cooling coil. The pressure is kept constant at 20 bar by means of a valve. An amount of offgas of 71.4 l is measured. The continued reaction time is 10 minutes. After the cooling and decompression of the autoclave, the product mixture is analysed by GC. After a one-stage distillation at 100-50 mbar and a maximum bottom temperature of 80° C., a further analysis is effected by means of GC. Table 10 shows the particular analysis results in GC area %.

TABLE 10

|  | 1,3-Buta-diene | 1,7-Octa-diene | 1,6-Octa-diene | 4-Vinyl-cyclohexene | N-Methyl-pyrrolidone | Further compounds |
|---|---|---|---|---|---|---|
| Reactor effluent | 1.7 | 77.6 | 2.5 | 0.6 | 17.6 | 0 |
| Distillate | 0 | 96.1 | 3.1 | 0.7 | 0 | 0.1 |
| Distillation bottoms | 0 | 6.1 | 0.2 | 0.3 | 92.1 | 1.3 |

The distillate obtained is 395.6 g of octadienes, which corresponds to an isolated yield of 85.5%. This gives rise to a catalyst productivity TON (octadienes)=72248. The purity based on 1,7-octadiene is 96.1%. The conversion of the formic acid is complete. It should be emphasized that, even in the case of long reaction times, no further isomerization of the 1,7-octadiene occurs in this preparation process.

Examples 8 and 11 show clearly that, in the case of use of N-oxyl radicals as stabilizers for 1,3-butadiene, for example 4-hydroxy-2,2,6,6-tetramethylpiperidine N-oxyl, even small amounts of catalyst of <50 ppm are sufficient. In contrast, Example 3 using the 4-tert-butylcatechol stabilizer for 1,3-butadiene and a catalyst amount of 50 ppm exhibits a significantly poorer yield.

EXAMPLE 12

45 ppm of Pd, isoprene stabilized with 100 ppm of
4-hydroxy-2,2,6,6-tetramethylpiperidine N-oxyl
based on 1,3-butadiene Under protective gas, 0.112 g of palladium acetate, 0.521 g of 1,3-bis(2,4,6-trimethylphenyl)imidazolium o-cresoxide-o-cresol and 0.27 g of sodium methoxide are dissolved in 200 g of freshly distilled N-methyl-pyrrolidone, and the mixture is stirred at 50° C. for 1 hour and then cooled to 20° C. Subsequently, 0.32 g of 4-hydroxy-2,2,6,6-tetramethylpiperidine N-oxyl (SiYPro C710 from Degussa AG) is added. This mixture is sucked into an evacuated 2 l autoclave from Büchi and then 606 g of freshly distilled isoprene (unstabilized) are sucked in. Thereafter, a pressure of 14 bar is applied by means of argon and the reactor is heated to 80° C. Within 240 minutes, 193 g of formic acid (98-100%) are metered in. After the reaction has set in, the temperature is kept between 80° C. and 81° C. with the aid of an internal cooling coil. The pressure is kept constant at 20 bar by means of a valve. An amount of offgas of 73.4 l is measured. The continued reaction time is 20 minutes. After the cooling and decompression of the autoclave, the product mixture is analysed by GC. After a one-stage distillation at 100-40 mbar and a maximum bottom temperature of 105° C., a further analysis is effected by means of GC. Table 11 shows the particular analysis results in GC area %.

The distillate obtained is 510.8 g of isomeric dimethyloctadienes, which corresponds to an isolated yield of 83.2%.

EXAMPLE 13

57 ppm of Pd, isoprene and 1,3-butadiene stabilized
with 100 ppm of
4-hydroxy-2,2,6,6-tetramethylpiperidine N-oxyl
based on 1,3-butadiene Under protective gas, 0.112 g of palladium acetate, 0.521 g of 1,3-bis(2,4,6-trimethylphenyl)imidazolium o-cresoxide-o-cresol and 0.27 g of sodium methoxide are dissolved in 200 g of freshly distilled N-methyl-pyrrolidone, and the mixture is stirred at 50° C. for 1 hour and then cooled to 20° C. Subsequently, 0.32 g of 4-hydroxy-2,2,6,6-tetramethylpiperidine N-oxyl (SiYPro C710 from Degussa AG) is added. This mixture is sucked into an evacuated 2 l autoclave from Büchi and then 303 g of freshly distilled isoprene (unstabilized) are sucked in. Thereafter, 240 g of 1,3-butadiene (unstabilized) are condensed in at −5° C. Then, a pressure of 14 bar is applied by means of argon and the reactor is heated to 80° C. Within 60 minutes, 193 g of formic acid (98-100%) are metered in. After the reaction has set in, the temperature is kept between 80° C. and 81° C. with the aid of an internal cooling coil. The pressure is kept constant at 20 bar by means of a valve. An amount of offgas of 79.2 l is measured. The continued reaction time is 20 minutes. After the cooling and decompression of the autoclave, the product mixture is analysed by GC. After a one-stage distillation at 100-40 mbar and a maximum bottom temperature of 105° C., a further analysis is effected by means of GC. Table 12 shows the particular analysis results in GC area %.

TABLE 12

|  | Isoprene/1,3-butadiene | Octa-diene | Methyl octa-diene | Di-methyl-octadiene | N-Methyl-pyrrolidone | Further compounds |
|---|---|---|---|---|---|---|
| Reactor effluent | 5.5 | 21.4 | 22.4 | 31.0 | 15.5 | 4.2 |
| Distillate | 0.1 | 26.5 | 27.6 | 39.4 | 0.8 | 5.6 |
| Distillation bottom | 0 | 0 | 0 | 0 | 97.6 | 2.4 |

The distillate obtained is a mixture of isomeric C8-C10 diolefins. These are mainly octadiene, methyloctadiene and dimethyloctadiene. 441.9 g are obtained as distillate, which corresponds to an isolated yield of 88.4% of hydrodimerization products.

TABLE 11

|  | Isoprene | Dimethyloctadiene 1 (Isomer 1) | Dimethyloctadiene 2 (Isomer 2) | Dimethyloctadiene 3 (Isomer 3) | N-Methyl-pyrrolidone | Further compounds |
|---|---|---|---|---|---|---|
| Reactor effluent | 11.1 | 40.1 | 30.9 | 4.1 | 12.7 | 1.1 |
| Distillate | 0 | 51.9 | 40.1 | 5.0 | 1.1 | 1.9 |
| Distillation bottoms | 0 | 0.2 | 1.5 | 1.3 | 94.8 | 2.2 |

EXAMPLE 14

Not inventive; 30 ppm of Pd, 1,3-butadiene stabilized with 100 ppm of 4-hydroxy-2,2,6,6-tetramethylpiperidine N-oxyl based on 1,3-butadiene Under protective gas, 0.056 g of palladium acetate, 0.521 g of 1,3-bis(2,4,6-trimethylphenyl)imidazolium o-cresoxide-o-cresol and 0.27 g of sodium methoxide are dissolved in 200 g of freshly distilled N-methyl-pyrrolidone, and the mixture is stirred at 50° C. for 1 hour and then cooled to 20° C. Subsequently, 0.32 g of 4-hydroxy-2,2,6,6-tetramethylpiperidine N-oxyl (SiYPro C710 from Degussa AG) is added. This mixture is sucked into an evacuated 2 l autoclave from Büchi and then 480 g of freshly distilled 1,3-butadiene (unstabilized) are condensed in at −5° C. The amount is measured by means of the weighing of the pressurized gas bottle. Thereafter, 202 g of formic acid (98-100%) are metered in with a pump. Subsequently, a pressure of 10 bar is applied by means of argon and the reactor is heated to 75° C. and stirred for 2 hours. The pressure is kept constant at 20 bar by means of a valve. During this time, no offgas evolution is observed. The continued reaction time is 30 minutes. After the cooling and decompression of the autoclave, the product mixture is analysed by GC. No 1,7-octadiene is detected in the reaction mixture.

The invention claimed is:

1. A process for preparing a substituted or unsubstituted 1,7-diolefin, comprising:
hydrodimerizing a non-cyclic olefin having at least two conjugated double bonds in a presence of a reducing agent and a catalyst,
wherein the reducing agent comprises at least one selected from the group consisting of formic acid and a formate, the reducing agent is metered in during a course of the hydrodimerizing of the non-cyclic olefin such that a ratio of the non-cyclic olefin to the reducing agent is from 1:1 to 10:1, and the catalyst comprises a metal-carbene complex which has a metal of group 8 to 10 of the Periodic Table and at least one carbene ligand of the structure 2

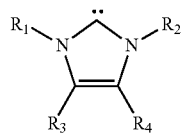

(2)

where:
$R_1$, $R_2$=—$(CH_2)_n$—B
B=mono- or polycyclic aryl group having 6 to 14 carbon atoms or mono- or polycyclic heterocycle having 5 to 14 carbon atoms and heteroatoms, where this heterocycle has 1 to 3 heteroatoms selected from the group consisting of N, O and S,
n=0-4 and
$R_3$ and $R_4$=substituents selected from the group consisting of hydrogen, alkyl, heteroaryl, aryl, —CN, —COOH, —COO-alkyl, —COO-aryl, —OCO-alkyl, OCO-aryl, —OCOO-alkyl, OCOO-aryl, —CHO, —CO-alkyl, —CO-aryl, —NH$_2$, —NH(alkyl), —N(alkyl)$_2$, NH(aryl), —N(aryl)$_2$, —F, —Cl, —Br, —I, —OH, —CF$_3$, —NO$_2$, -ferrocenyl, —SO$_3$H, and —PO$_3$H$_2$,
where the alkyl groups have 1 to 12 carbon atoms and the aryl groups 5 to 14 carbon atoms, and the substituents of $R_3$ and $R_4$ may also be part of a bridging aliphatic or aromatic ring,
and the substituents of $R_1$ and $R_2$ are the same or different and are substituted or unsubstituted, and the substituents of $R_3$ and $R_4$ are the same or different and are substituted or unsubstituted.

2. The process according to claim 1,
wherein the metal-carbene complex comprises at least one metal selected from the group consisting of nickel, rhodium, palladium and platinum.

3. The process according to claim 2,
wherein the metal-carbene complex has palladium as the metal.

4. The process according to claim 1,
wherein the metal-carbene complex comprises at least one carbene ligand of the structure 2 where $R_3$ and $R_4$ are each hydrogen.

5. The process according to claim 4,
wherein the metal-carbene complex comprises at least one carbene ligand of the structure 2 where $R_3$ and $R_4$ are each hydrogen and $R_1$ and $R_2$, where n=0, and B are each a phenyl or 2,4,6-trimethylphenyl group.

6. The process according to claim 4, wherein the at least one carbene ligand consists of a carbene ligand of the structure 2 which satisfies that $R_3$ and $R_4$ are each hydrogen and $R_1$ and $R_2$, where n=0, and B are each a 2,4,6-trimethylphenyl group.

7. The process according to claim 4, wherein the at least one carbene ligand consists of a carbene ligand of the structure 2 which satisfies that $R_3$ and $R_4$ are each hydrogen and $R_1$ and $R_2$, where n=0, and B are each a phenyl group.

8. The process according to claim 1,
wherein the catalyst comprises 1 to 500 ppm by mass of a metal based on an overall mass of a reaction mixture, at a start of the hydrodimerizing.

9. The process according to claim 1,
wherein the non-cyclic olefins having at least two conjugated double bonds are compounds selected from the group consisting of 1,3-butadiene, isoprene, 1,3-pentadiene, chloroprene, and corresponding mixtures which comprise non-cyclic olefins with at least two conjugated double bonds.

10. The process according to claim 9,
wherein the non-cyclic olefin comprises 1,3-butadiene.

11. The process according to claim 1,
wherein non-cyclic olefins either have no stabilizer or have a stabilizer comprising one of alkylated phenols and stable N-oxyl radicals.

12. The process according to claim 11,
wherein the non-cyclic olefins comprise a free radical stabilizer comprising one of alkylated phenols and stable N-oxyl radicals.

13. The process according to claim 12,
wherein the N-oxyl radicals are selected from the group consisting of 4-hydroxy-2,2,6,6-tetramethylpiperidine N-oxyl and 2,2,6,6-tetramethylpiperidine N-oxyl.

14. The process according to claim 1,
wherein the reducing agent comprises formic acid and the formate.

15. The process according to claim 14,
wherein the reducing agent comprises formate.

16. The process according to claim 1,
wherein the reducing agent is formic acid.

17. The process according to claim 1,
wherein the reducing agent comprises at least one selected from the group consisting of ammonium formate, triethylammonium formate, trimethyl-ammonium formate, tripropylammonium formate, lithium formate, sodium formate, potassium formate, magnesium formate, and calcium formate.

18. The process according to claim 1,
wherein the hydrodimerizing of the non-cyclic olefins is performed in a presence of bases.

19. The process according to claim 18,
wherein the bases are selected from the group consisting of alkali metal hydroxides, alkali metal alkoxides and tertiary amines.

20. The process according to claim 1, wherein the non-cyclic olefins comprise a free radical stabilizer comprising at least one stable N-oxyl radical.

21. The process according to claim 1, wherein the catalyst comprises 1 to 50 ppm by mass of the metal based on the overall mass of the reaction mixture, at the start of the hydrodimerizing.

22. The process according to claim 21, wherein the at least one carbene ligand consists of a carbene ligand of the structure 2 which satisfies that $R_3$ and $R_4$ are each hydrogen and $R_1$ and $R_2$, where n=0, and B are each a 2,4,6-trimethylphenyl group.

\* \* \* \* \*